(12) United States Patent
Konesky et al.

(10) Patent No.: US 8,795,265 B2
(45) Date of Patent: Aug. 5, 2014

(54) ELECTROSURGICAL APPARATUS TO GENERATE A DUAL PLASMA STREAM AND METHOD THEREOF

(75) Inventors: Gregory A. Konesky, Hampton Bays, NY (US); Borislav S. Simeonov, St. Petersburg, FL (US)

(73) Assignee: Bovie Medical Corporation, Clearwater, FL (US)

( * ) Notice: Subject to any disclaimer, the term of this patent is extended or adjusted under 35 U.S.C. 154(b) by 775 days.

(21) Appl. No.: 13/015,834

(22) Filed: Jan. 28, 2011

(65) Prior Publication Data

US 2011/0184408 A1 Jul. 28, 2011

Related U.S. Application Data

(60) Provisional application No. 61/298,982, filed on Jan. 28, 2010.

(51) Int. Cl.
 *A61B 18/04* (2006.01)
 *A61B 18/00* (2006.01)
 *A61B 18/12* (2006.01)

(52) U.S. Cl.
 CPC ..... *A61B 18/042* (2013.01); *A61B 2018/00559* (2013.01); *A61B 2018/00577* (2013.01); *A61B 18/1206* (2013.01)

USPC ............................................. 606/27; 606/41

(58) Field of Classification Search
 USPC ................................. 606/27, 34, 41
 See application file for complete search history.

(56) References Cited

U.S. PATENT DOCUMENTS

| | | | |
|---|---|---|---|
| 5,720,745 A * | 2/1998 | Farin et al. | 606/49 |
| 6,629,974 B2 * | 10/2003 | Penny et al. | 606/41 |
| 6,890,332 B2 * | 5/2005 | Truckai et al. | 606/41 |
| 8,388,615 B2 * | 3/2013 | Bystryak et al. | 606/34 |

* cited by examiner

*Primary Examiner* — Michael Peffley
*Assistant Examiner* — Daniel Fowler
(74) *Attorney, Agent, or Firm* — Michael J. Porco; Gerald E. Hespos; Matthew T. Hespos

(57) ABSTRACT

The present disclosure relates to an electrosurgical apparatus to generate a dual plasma stream to perform electrosurgery on a surgical site on a patient. The apparatus and method of the present disclosure generates a hot gas jet to a surgical site by generating two plasma beams that are electrically up to 180 degrees out of phase from each other. Since each beam uses the other beam to establish plasma currents at a load, the combined dual plasma stream can be used on non-conductive surfaces, e.g., a tissue at the surgical site. Furthermore, by applying different flow rates to the plasma beams, various scanning effects by the hot gas jet can be achieved.

30 Claims, 8 Drawing Sheets

ELECTROSURGICAL APPARATUS TO GENERATE A DUAL PLASMA STREAM AND METHOD THEREOF

PRIORITY

This application claims priority to U.S. Provisional Patent Application Ser. No. 61/298,982 filed on Jan. 28, 2010, the contents of which are hereby incorporated by reference in its entirety.

BACKGROUND

1. Field

The present disclosure relates generally to electrosurgery and electrosurgical systems and apparatuses, and more particularly, to an electrosurgical apparatus to generate a dual plasma stream and method thereof.

2. Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Plasma jets can broadly be grouped into "Local" and "Remote" types. FIG. 9 illustrates exemplary plasma generators including a source of electrosurgical energy 402, a gas supply 404 and a handpiece 406. As shown in FIG. 9A, in local plasma jets, the primary discharge 408 occurs entirely within the hand piece 406, and the flowing inert gas 410 draws out only the most long-lived radical molecules and activated or ionized atoms. Consequently, it provides the weakest effect on the target surface 412, but since no current flows to or from that surface, an insulating surface is suitable. FIG. 9A illustrates a capacitively coupled and inductively coupled plasma jet.

In remote plasma jets, as shown in FIG. 9B, the plasma discharge 408 extends from the hand piece 406 all the way to the target surface 414, and so is said to be "remote" to the hand piece 406. Since the discharge 408 touches the target surface 414, short-lived, highly energetic radicals and ions are present at the surface, providing a very strong effect. The drawback is that the surface 414 must be conductive, and have sufficient electrical capacitance to accommodate the displacement currents that support the remote plasma discharge. For example, using J-Plasma on a mouse will require a return pad to increase the overall equivalent capacitance, while on a person of significant size, no return pad is needed.

Therefore, a need exists for techniques to generate plasma for surgical applications where the plasma will have a strong effect at the surgical site while not requiring a conductive surface or return pad.

SUMMARY

The present disclosure relates to an electrosurgical apparatus to generate a dual plasma stream to perform electrosurgery on a surgical site on a patient. The apparatus and method of the present disclosure provides a dual plasma stream to a surgical site by generating two plasma beams that are electrically up to 180 degrees out of phase from each other. Since each beam uses the other beam to establish plasma currents at a load, the combined dual plasma stream can be used on non-conductive surfaces, e.g., a tissue at the surgical site. The dual beam approach of the present disclosure permits the use of a non-conductive surface, or one with a very small equivalent capacitance, yet maintain the strong effect of a remote plasma discharge. Furthermore, no grounding is needed.

The electrosurgical apparatus comprises an electrosurgical generator coupled to an electrical power source to supply power for the electrosurgical apparatus and a plasma generator including two electrodes operatively coupled to the electrosurgical generator to selectively receive electrical energy therefrom and to generate the plasma stream. A noble gas conduit coupled to a noble gas source to feed noble gas such as helium or argon to the noble gas conduit surrounds each of the two electrodes to at least partially ionize the noble gas to create the plasma stream. A flow controller is further provided to modulate and/or pulse the flow of the carrier or noble gas from the gas source to each of the gas conduits.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
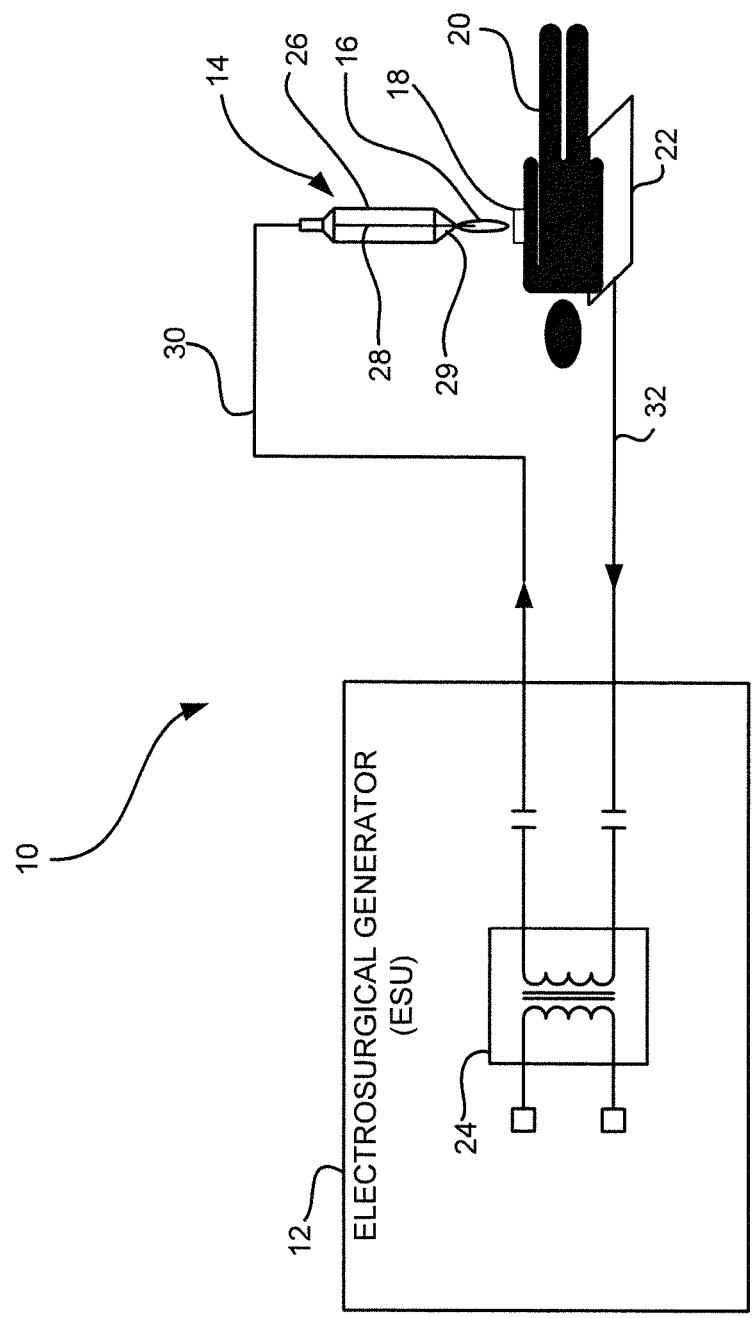
FIG. 1 is an illustration of a monopolar electrosurgical system in accordance with an embodiment of the present disclosure.

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

The present disclosure relates to an electrosurgical apparatus to generate a plasma stream to perform electrosurgery on a surgical site on a patient. As described more fully hereinafter, the electrosurgical apparatus comprises an electrosurgical generator to supply power to the electrosurgical device and a plasma generator operatively coupled to the electrosurgical generator to receive electrical power therefrom and to generate a plasma stream for application to a surgical site or target area on a patient.

The present disclosure provides an electrosurgical apparatus to generate a dual plasma stream to perform electrosurgery on a surgical site on a patient. The apparatus and method of the present disclosure provides a dual plasma stream to a surgical site by generating two plasma beams that are electrically up to 180 degrees out of phase from each other. Since each beam uses the other beam to establish plasma currents at a load, the combined dual plasma stream can be used on non-conductive surfaces, e.g., a tissue at the surgical site. It is to be appreciated that the term "electrically up to 180 degrees out of phase" refers to the driving voltage waveforms at each electrode generating the respective plasma beams or jets, although the current waveforms are also up to 180 degrees out of phase relative to each other.

FIG. 1 shows a monopolar electrosurgical apparatus generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively, "active electrode") in the handpiece 26 to create the plasma stream 16 for application to the surgical site 18 on the patient 20.

The return path to the electrosurgical generator 12 is through the tissue and body fluid of the patient 20, the conductor plate or support member 22 and a return conductor 32 (collectively, "return electrode") to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

Figure 2:
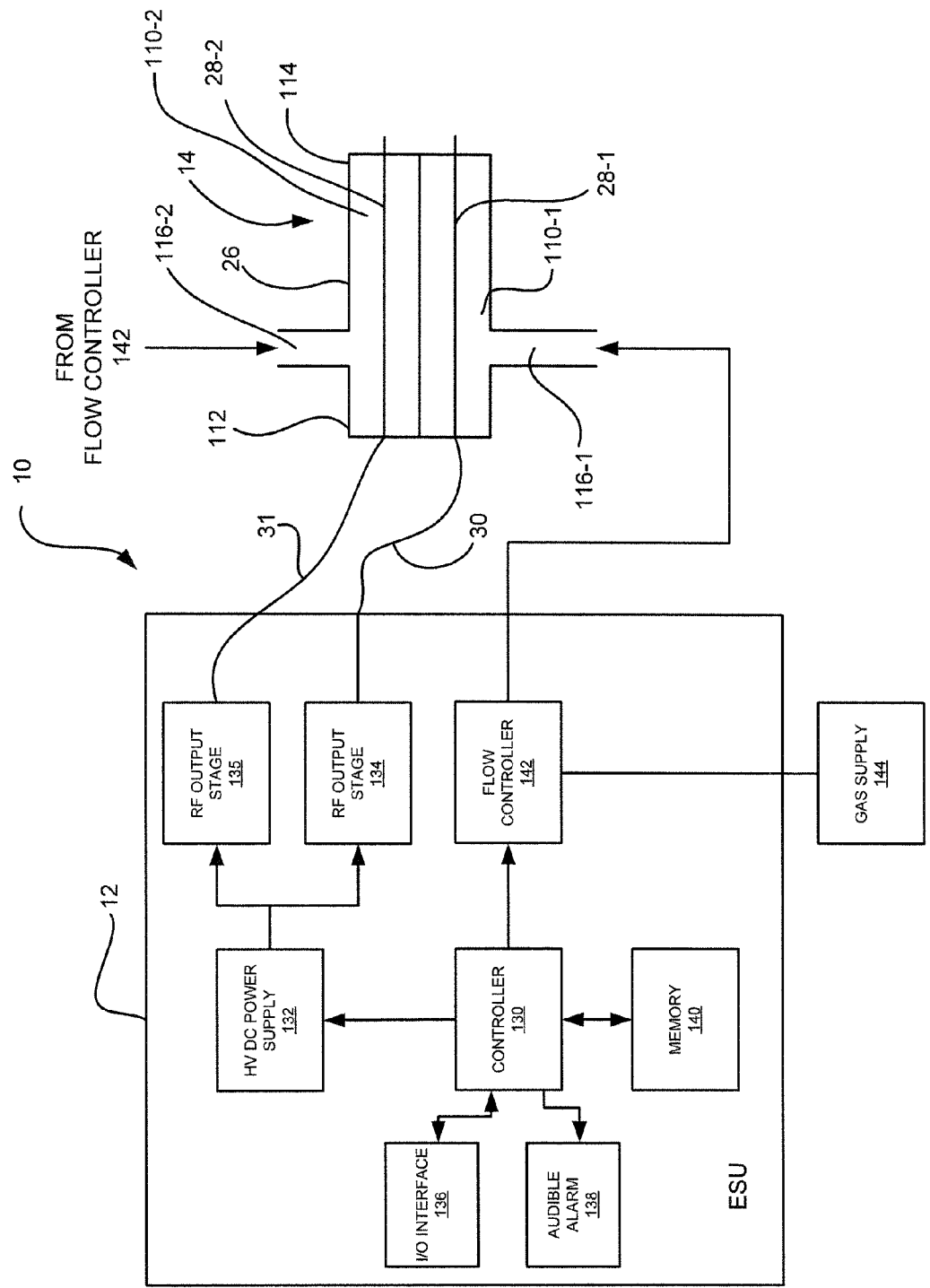
FIG. 2 is a block diagram of an electrosurgical generator and a plasma generator in accordance with an embodiment of the present disclosure.

Referring to FIG. 2, the electrosurgical generator 12 and a plasma generator 14 including a first and second electrodes 28-1, 28-2 supported by the handpiece 26 and at least partially disposed in the fluid flow housing 29 is illustrated. The first and second electrodes 28-1, 28-2 are each concentrically disposed within an inner noble gas conduit 110-1, 110-2 respectively, each conduit 110-1, 110-2 having a proximal end 112 and a distal end 114. Furthermore, each noble gas conduit 110-1, 110-2 is coupled to a noble gas source 144 by a noble gas supply conduit 116-1, 116-2 to feed noble gas such as helium or argon to the individual noble gas conduits 110-1, 110-2. The conducting plasma stream 16 couples the electrosurgical generator 12 to the patient 20, the details of which will be described below in relation to FIGS. 3 and 4.

The electrosurgical generator 12 includes a controller 130 that controls a HV DC power supply 132 to supply electrosurgical energy being output from RF output stages 134, 135. The first RF output stage 134 is coupled to first electrode 28-1 by conductor 30 and the second RF output stage 135 is coupled to the second electrode 28-2 by conductor 31. The first and second RF output stages 134, 135 produce electrosurgical energy wherein each output from the respective RF output stage is up to 180 degree out of phase from each other. It is to be appreciated that the two RF output stages may be constructed in numerous ways to achieve two separate outputs being up to 180 degrees out of phase and the specific construction is not crucial to the teachings of the present disclosure. In one embodiment, each RF output stage includes an adjustable oscillating circuit where the phase angle of each circuit is separately adjustable. In another embodiment, a master oscillator is provided which directly feeds one of the output stages and then also feeds a variable delay line or circuit to provide phase shifts that are adjustable from 0 to 180 degrees. The phase shifted output of the delay line or circuit then feeds the other output stage. In a further embodiment, each RF output stage includes a transformer where the secondary windings of one of the transformers is reversed; however, in this embodiment, the phase shift is not adjustable and the resulting phase shift is fixed at 180 degrees.

The electrosurgical generator 12 will indicate various operating conditions to an operator via an I/O interface 136 or an audible alarm 138. The I/O interface can be in any known form and may include a touch screen, knobs, LCD display, LEDs, buttons, dials, etc. or any combination thereof. In one embodiment, the I/O interface will be utilized by a user to set or adjust various parameters of the RF output stages, e.g., power level and phase angle, among others.

It is to be appreciated that conductors 30 and 31 may be constructed in a single cable including a single connector for coupling to an appropriate port on the generator 12. In one embodiment, the generator 12 will include two ports for coupling the conductors 30, 31 to the generator 12. In this embodiment, each output port is separately controllable via the I/O interface 136. In this manner, the generator 12 of the present disclosure may also be useable with a single beam plasma generator, where the single beam plasma generator is coupled to one port and the other port is shut off or disabled.

The apparatus 10 further includes a flow controller 142 for controlling the flow of gas to the plasma generator 14. The flow controller 142 modulates or pulses the flow of gas from the gas supply 144 to the plasma generator 14. The flow controller 142 is coupled to the controller 130 and receives control signals from the controller 130 based on user input via I/O interface 136 or based on an algorithm or software function stored in memory 140. Although in the embodiment shown the flow controller 142 is disposed in the electrosurgical generator 12, the flow controller 142 can be located external to the electrosurgical generator 12 and disposed in a separate housing. It is to be appreciated that if an external flow controller 142 is employed, the external flow controller 142 will be controlled by controller 130 so that a single source will control the flow of gas and the supply of electrosurgical energy.

Figure 4:
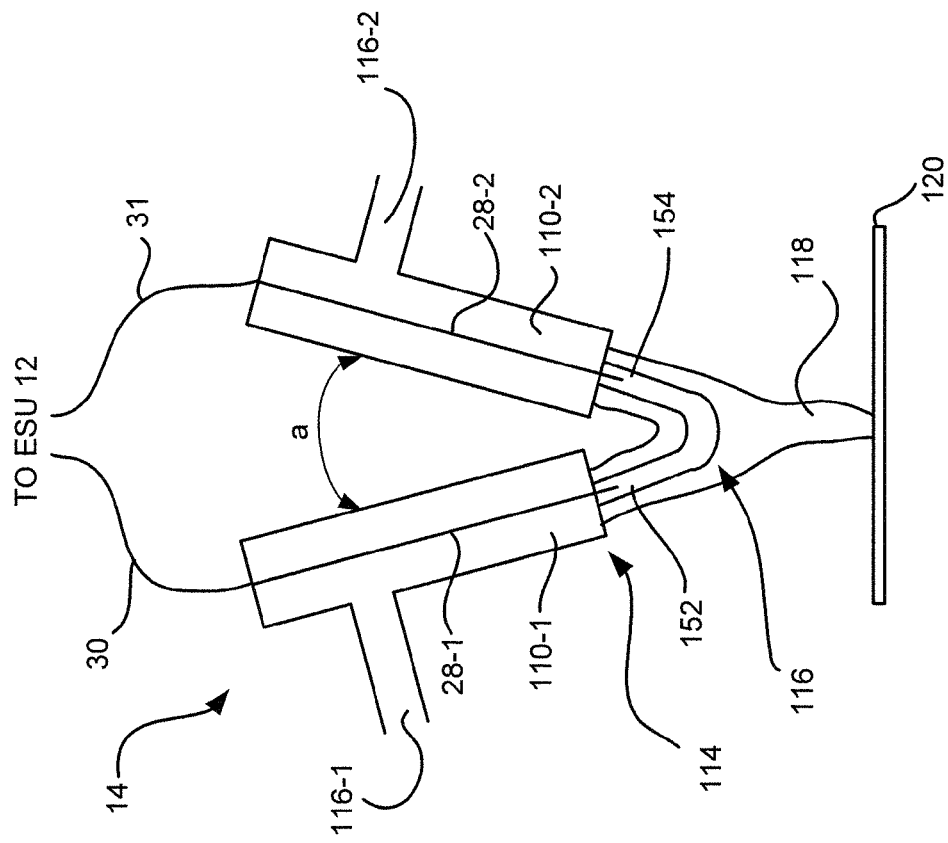
FIG. 4 is an illustration of two interacting or dueling plasma beams where two plasma generators are disposed at a predetermined angle from each other in accordance with embodiment of the present disclosure.
Figure 3:
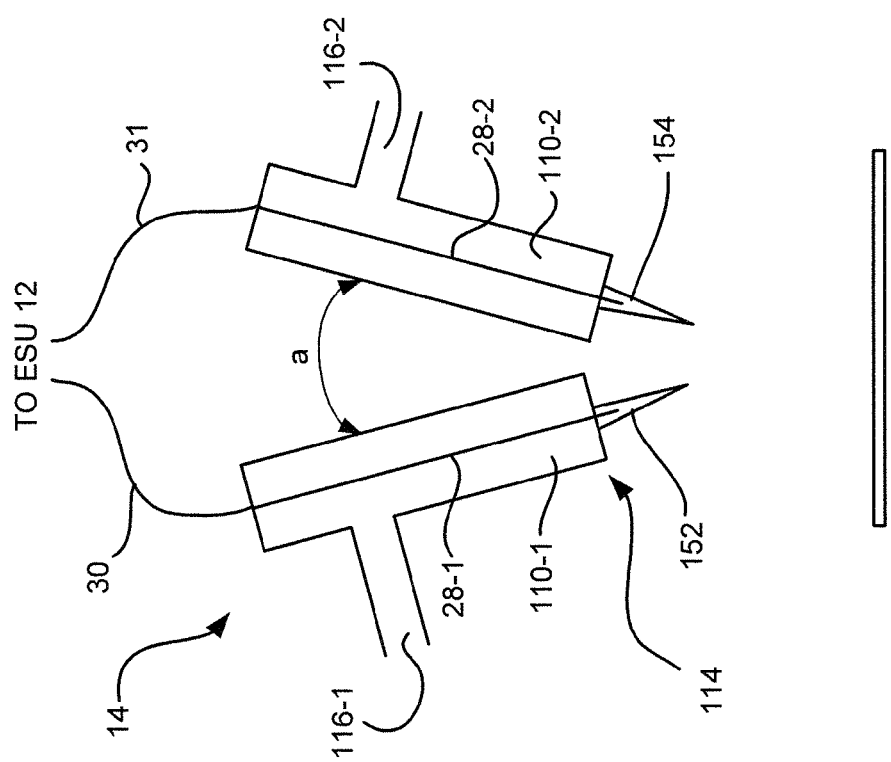
FIG. 3 is an illustration of two plasma beams being generated upon initiation in accordance with an embodiment of the present disclosure.

Referring to FIGS. 3 and 4, an illustration of two interacting or dueling plasma beams in accordance with an embodiment of the present disclosure is provided. Each respective combination of electrode and gas conduit, e.g., 28-1, 110-1 and 28-2, 110-2, will emit a plasma beam from the distal end 114 of the plasma generator 14. For example, the first electrode 28-1 and gas conduit 110-1 will emit plasma beam 152 upon initiation and, likewise, the second electrode 28-2 and gas conduit 110-2 will emit plasma 154 upon initiation, as illustrated in FIG. 3. After initiation of each beam 152, 154, the beams will cross and interact to form joint plasma discharge 116. In addition to UV and ozone, a combined jet of very hot gas 118 is formed at the joint plasma discharge 116, as shown in FIG. 4. The conduits 110-1, 110-2 direct the flow of gas and thus the direction of the individual plasma beams 152, 154. Different effects can be achieved by arranging the individual beams at different angles. As can be seen in FIG. 4, the gas conduits 110-1 and 110-2 are adjustable relative to each other and can be set at a predetermined angle a. What defines the predetermined angle a depends on the geometry and the length of the two plasma jets. Plasma jets that are widely spaced must be pointed at a wide angle for them to cross, while jets that are close to each other only need a shallow angle before they meet. Similarly, long plasma jets (high output power and gas flow rate) need a much smaller angle before the tips meet, while short plasma jets will need a larger angle. As the angle between the two beams widens, the hot gas jet becomes more diffuse and less well-defined, until the limiting case of 180 degrees, where the two plasma jets are pointing directly at each other, and the hot gas simply "splashes" out sideways.

The resulting hot gas jet 118 will interact with the surgical site 120 to produce a desired effect, e.g., ablation, without the requirement of a conductive surface. Furthermore, since no currents are flowing into the target tissue (i.e., neither displacement nor return currents), the techniques of the present disclosure are beneficial in applications on the spine, brain, heart, neurological, etc., since no interfering electrical signals would be imposed by the procedure.

Figure 5:
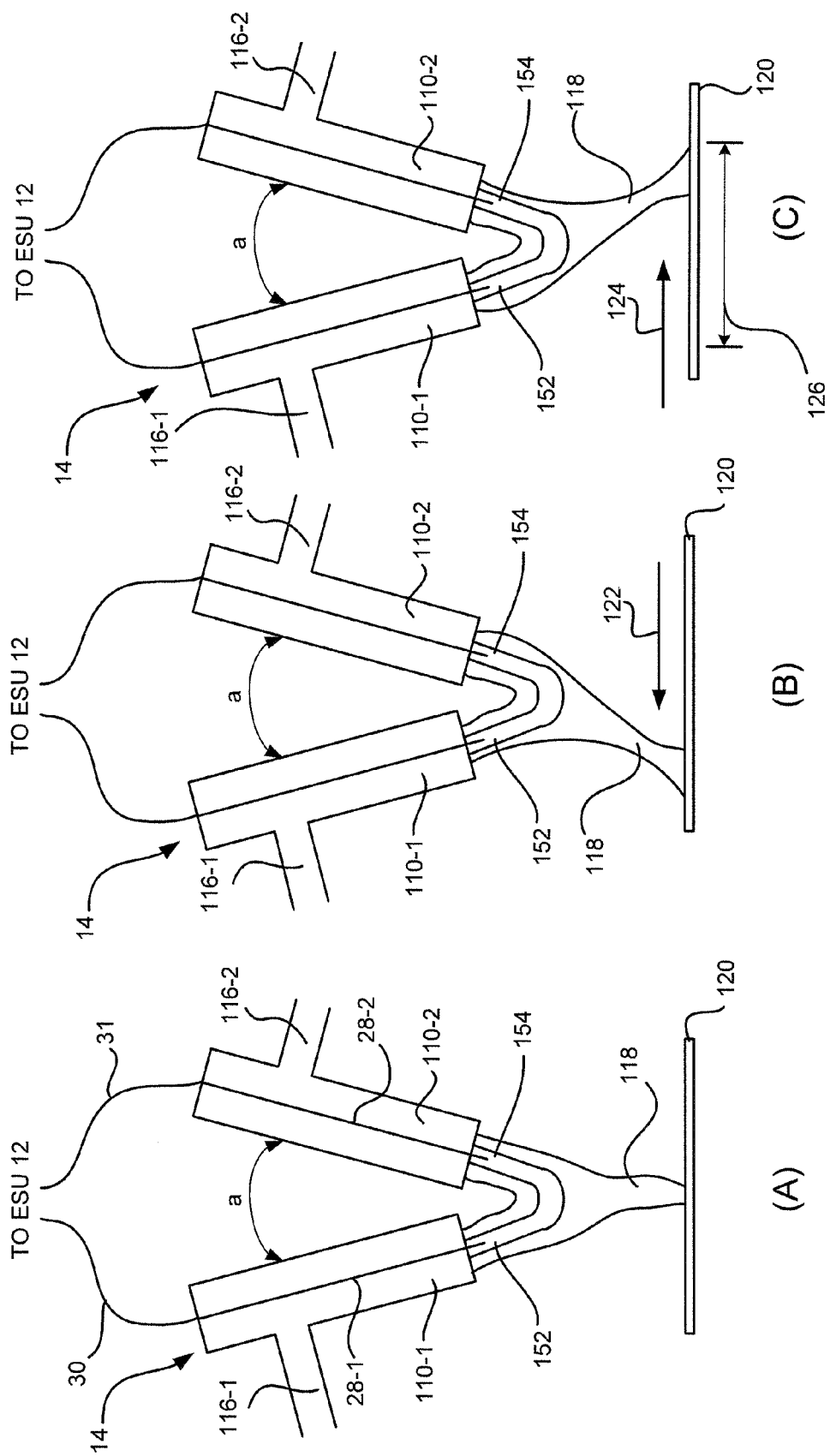
FIG. 5 illustrates a hot gas scanning application employing a plasma generator in accordance with an embodiment of the present disclosure.

In another embodiment of the present disclosure, the gas supplied to the gas conduits 110-1, 110-2 will be modulated to create a scanning hot gas jet 118 as will be described in relation to FIG. 5. Referring to FIG. 5(A), a hot gas jet 118 is generated as described above. Here, the gas conduits 110-1, 110-2 are arranged at approximately 30 degrees relative to each other and the noble gas supplied via supply conduits 116-1, 116-2 is supplied at the same rate to both gas conduits 110-1, 110-2. The resultant hot gas jet 118 is formed generally between the two gas conduits 110-1, 110-2.

By modulating the flow of gas in one of the gas conduits, the hot gas jet 118 will now point to one side, away from the stronger plasma jet gas flow and towards the weaker one. If the relative flow rates of the two plasma jets are periodically varied, the hot gas jet 118 will scan back and forth in a linear direction. For example, in FIG. 5(B), the gas supplied to conduit 110-2 is at a greater flow rate than the gas supplied to conduit 110-1. This causes the gas jet 118 to move in the direction of arrow 122. If the gas is now modulated so that the gas flow through conduit 110-1 is greater than the rate of flow through conduit 110-2, the gas jet moves in the direction of arrow 124, as shown in FIG. 5(C). By modulating the gas flow in this manner, the hot gas jet 118 will scan back and forth and cover a large surface area as indicated by 126 without moving the plasma generator 14.

It is to be appreciated that the modulation of the supplied gas to cause the hot gas jet to scan back and forth can be implemented in various ways. In one embodiment, a modulating valve can be coupled between the gas supply conduits 116-1, 116-2 and the gas supply. In this embodiment, controller 130 or flow controller 142 will modulate the valves to the desired flow rates, i.e., the flow rate in one conduit to be greater than the other and vice versa. In another embodiment, the rate of flow to one of the gas conduits 110-1, 110-2 will be fixed and the gas flow rate of the other conduit will be modulated above and below the fixed flow rate to achieve the scanning effect described above. It is to be appreciated that the modulating valves may be disposed in the electrosurgical generator 12 or in the handpiece 26.

The above-described scanning application of the plasma generator may be useful in an endoscopic application where there is limited range of motion of the applicator (e.g., plasma generator 14), but the hot gas jet can be independently steered along the plane of the two jets.

Figure 6:
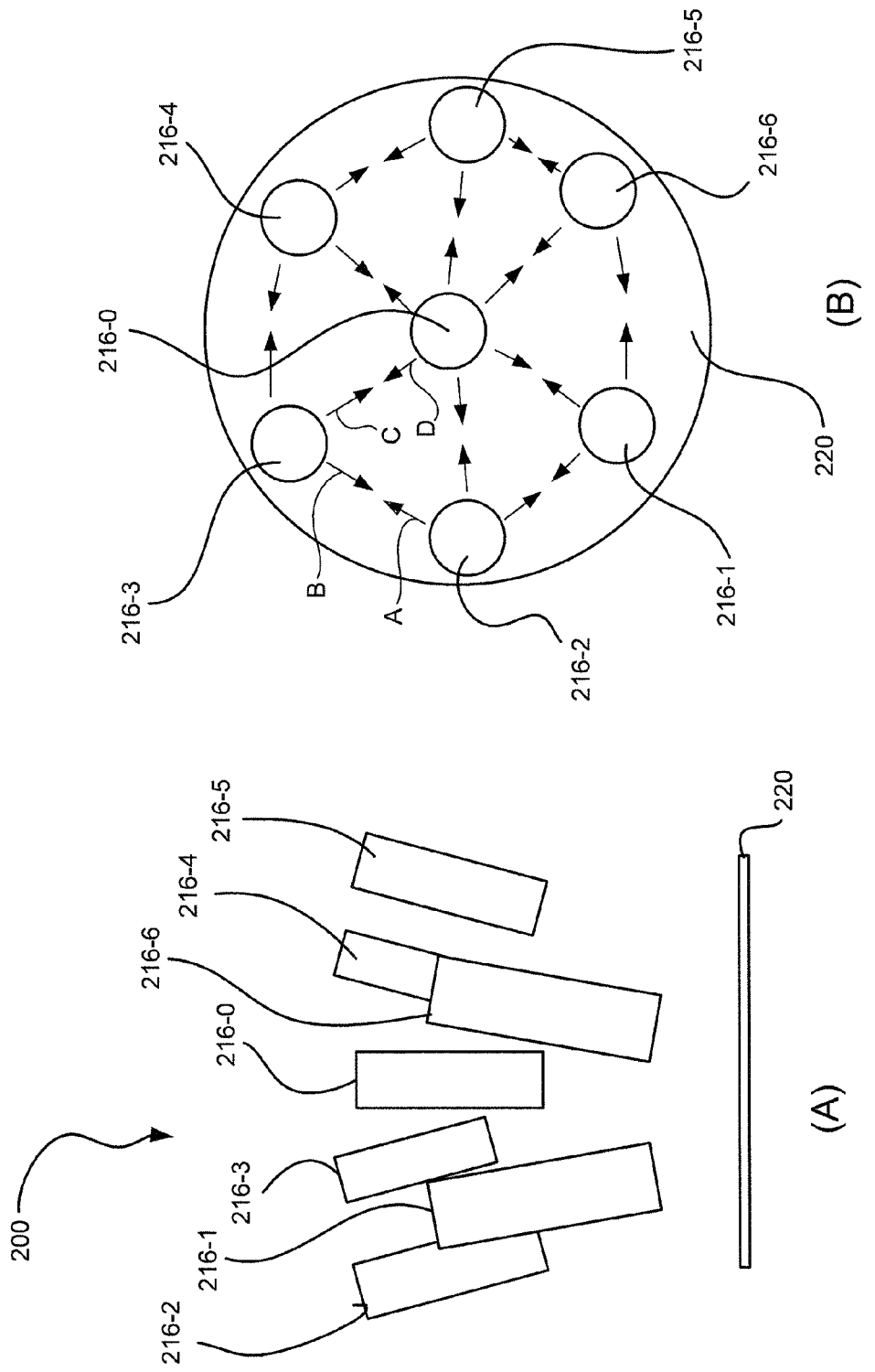
FIG. 6A is a side view of a distal end of a plasma generator including a plurality of gas conduits.
FIG. 6B is a view illustrating a coverage area of the plasma generator shown in FIG. 6A.

In another embodiment, the plasma generator can be configured to implement a wide area paint-brush type of application. Such an embodiment is shown in FIG. 6, where FIG. 6A is a side view of a distal end of a plasma generator 200 having a plurality of gas conduits 216-0 through 216-6. Other structures such as electrodes disposed in each gas conduct have been removed for clarity.

Referring to FIG. 6A, a centrally disposed gas conduit 216-0 is surrounded by, in this example, six gas conduits 216-1 through 216-6. Although not shown, each gas conduit will have an electrode disposed within the gas conduit as in the above-described embodiment. In one embodiment, the centrally disposed gas conduit 216-0 is concentric with the handpiece of the plasma generator and each of the surrounding gas conduits are slightly biased toward the central longitudinal axis of the handpiece. In the embodiment shown in FIG. 6, any two adjacent gas conduits may have their electrodes energized at one time with the gas flow rate to the gas conduits modulated to create a scanning hot jet of gas as described above in relation to FIG. 5.

Referring to FIG. 6B, arrows represent the scan lines along a surface of a surgical site 220. For example, arrows A and B indicate a line scanned with hot gas by energizing the electrodes disposed within gas conduits 216-2 and 216-3 and subsequently modulating the gas flow rate therein. Likewise, arrows C and D indicate a line scanned between gas conduits 216-3 and 216-0. By sequentially activating all adjacent gas conduit pairs, all of the surface indicated by arrows on surgical site 220 will be treated by the hot gas jet.

Figure 7:
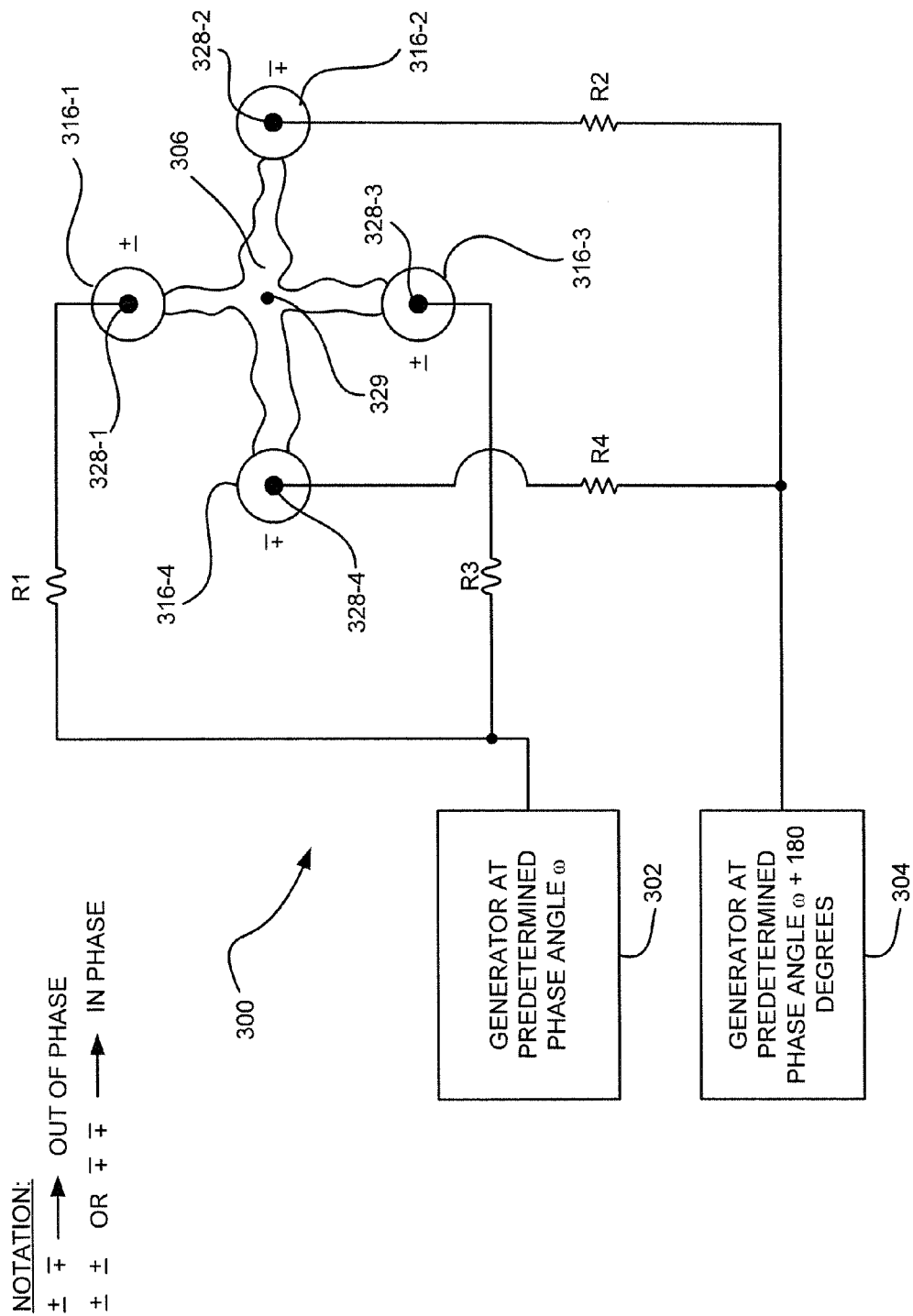
FIG. 7 is a schematic diagram of a plasma generator having a plurality of gas conduits activated simultaneously.

Referring to FIG. 7, another embodiment of a plasma generator 300 is illustrated. In this embodiment, as described above, the generator includes a first output stage 302 at a predetermined phase angle ω and a second output stage 304 at a predetermined phase angle ω+180 degrees. It is to be appreciated that the phase shift from the second output stage 304 does not have to be exactly 180 degrees but can be a range of values up to 180 degrees. The first output stage 302 is coupled to electrodes 328-1 and 328-3 (forming a first electrode pair) disposed within gas conduits 316-1 and 316-3 (forming a first gas conduit pair) via current limiting components R1 and R3. The second output stage 304 is coupled to an electrodes 328-2 and 328-4 (forming a second electrode pair) disposed within gas conduits 316-2 and 316-4 (forming a second gas conduit pair) via current limiting components R2 and R4. Each gas conduit of the gas conduit pairs is arranged diametrically opposite the other gas conduit of the gas conduit pair about a central point 329. The electrodes are energized simultaneously forming a cross-shaped plasma beam 306 with a hot gas jet formed approximately below central point 329 (not shown) in the general direction of the gas glow. By modulating the gas flow rates through gas conduits 316-1, 316-2, 316-3 and 316-4, different scanning patterns can achieved. While resistors are shown for components R1-R4, other current limiting components, such as capacitors, inductors, etc., or combinations thereof, can be used.

Figure 8A:
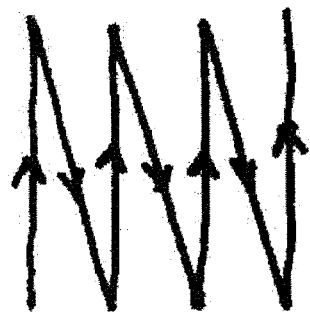
FIG. 8A illustrates differential gas flow rates for the plasma generator shown in FIG. 7 and the resulting two-dimensional (2D) scan in accordance with an embodiment of the present disclosure.
Figure 8A:
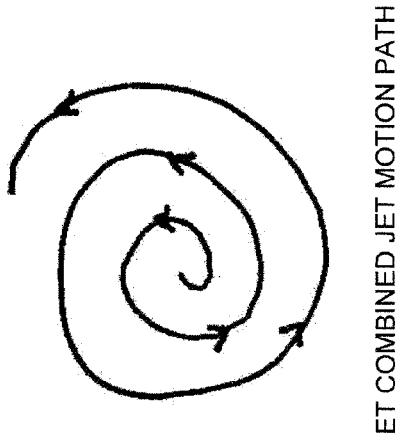

For example, referring to the left portion of FIG. 8A, a graph for differential gas flow rates to be applied to the gas conduits are shown. The upper part of the graph shows the gas flow to be applied to gas conduits 316-1 and 316-3 to cause the gas jet to move in an up-down direction, e.g., a triangular gas flow waveform, while the lower portion of the graph illustrates the gas flow applied to gas conduits 316-2 and 316-4 to cause the gas jet to move left-right. It is to be appreciated that the triangular gas flow waveform being applied to gas conduits 316-2 and 316-4 (i.e., the horizontal sweep frequency) is a multiple of the triangular gas flow waveform being applied to gas conduits 316-1 and 316-3 (i.e., the vertical sweep frequency). The right portion of FIG. 8A illustrates the net result of the combined plasma jet motion, i.e., a two-dimensional 2D raster scan. As can be seen, the raster scan can cover a rectangular surface area, where the spacing between the diagonally scan lines can be varied by varying the amplitudes of the gas flow applied to the gas conduits.

Figure 8B:
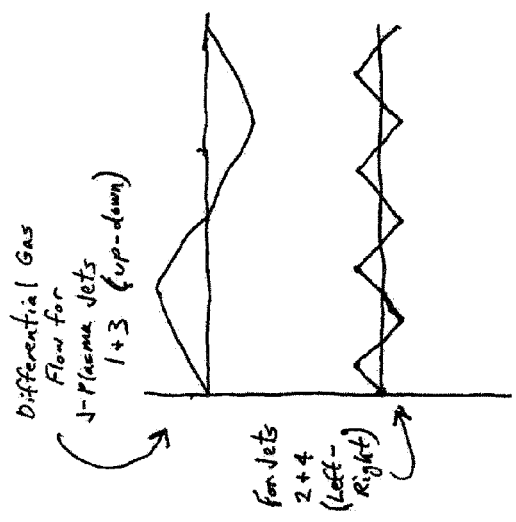
FIG. 8B illustrates differential gas flow rates for the plasma generator shown in FIG. 7 and the resulting two-dimensional (2D) scan in accordance with another embodiment of the present disclosure.
Figure 8B:
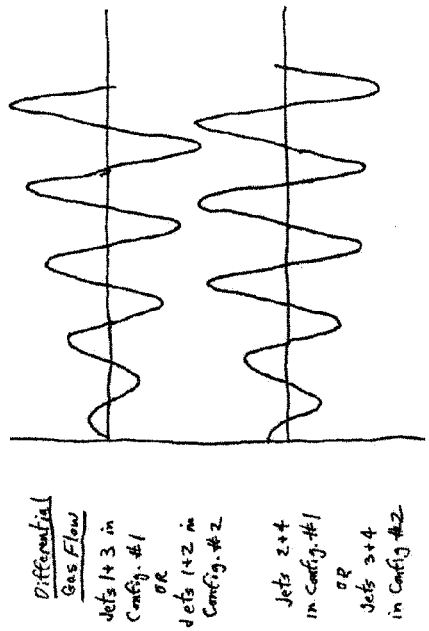
Figure 9:
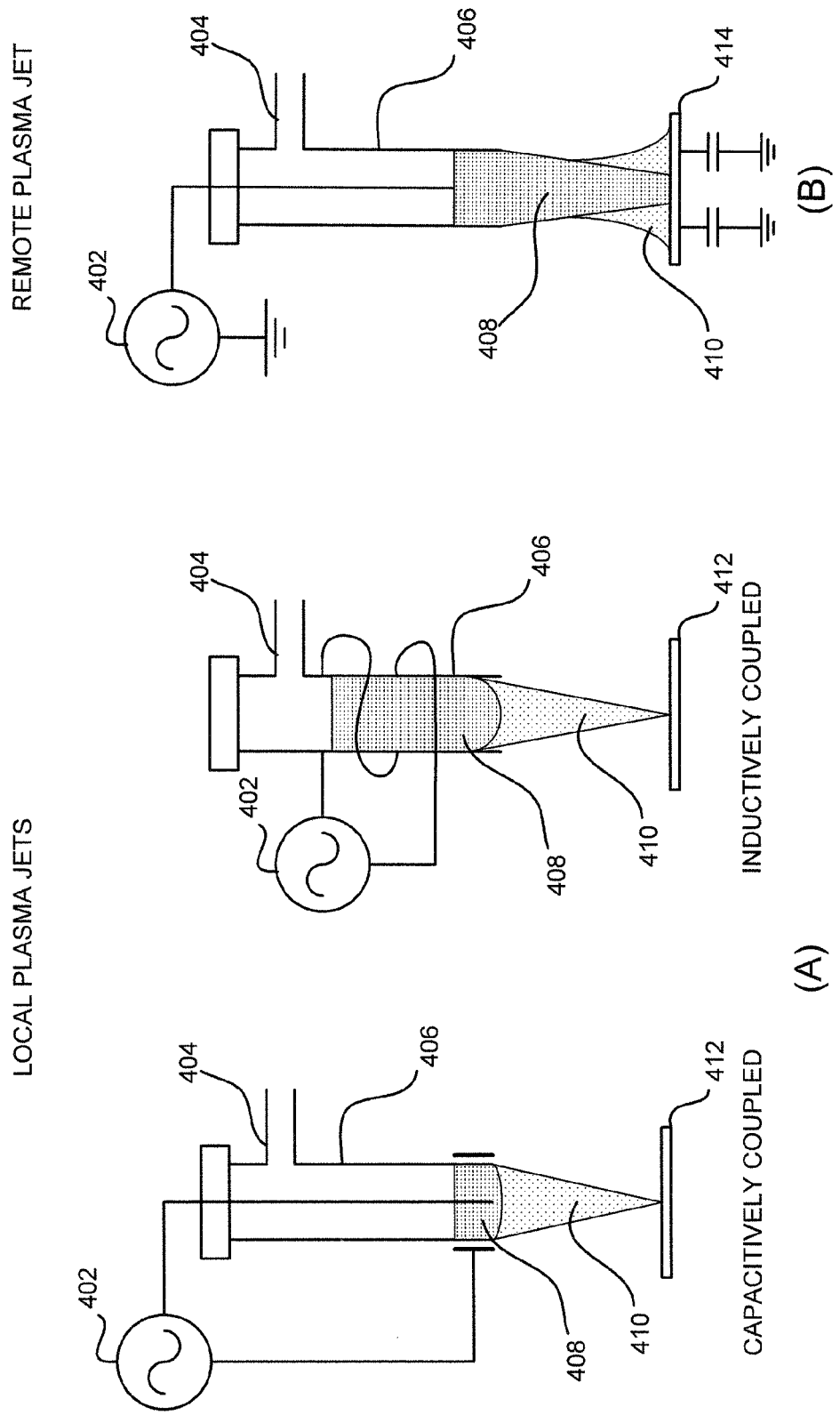
FIG. 9 illustrates various conventional plasma applications.

FIG. 8B illustrates another example where the modulation of gas flow rates creates a circular net combined gas jet motion path. In this embodiment, the gas flow applied to the gas conduits are sine waves of increasing amplitude, with one pair of gas conduits at a 90 degrees phase shift in differential gas flow waveform. For example, a gas flow rate applied as a sine wave of increasing amplitude may be applied to gas conduits 316-1 and 316-3, while the gas flow applied to gas conduits 316-2 and 316-4 is the same sine wave of increasing amplitude but shifted at 90 degrees. The resulting jet motion path starts at a central point of the four gas conduits, e.g., in the cross hair of the gas conduits, and increasingly spirals outward as indicated by the arrows in the net combined jet motion path illustrated in the right portion of FIG. 8B. In this embodiment, a circular surface area of targeted tissue can be treated, while keeping the plasma generator stationary. It is to be appreciated that the different effects can be achieved by varying the gas flow waveforms shown. For example, by varying the duration of each cycle of the sine wave, the total time to achieve the circular combined path can be varied.

In another embodiment, a plasma generator may be configured to employ several of the structures shown in FIG. 7. For example, to cover a large surface area, the plasma generator may include four of the dual gas conduit pairs arranged to cover a rectangular surface area which would be the sum of four raster scans as shown in FIG. 8A. This is merely an illustrative example and in no way is meant to limit the number of dual gas conduit pairs that may be employed in a single plasma generator.

It is further to be appreciated that many other configurations in accordance with the teachings of the present disclosure are contemplated to be within the scope of this disclosure. For example, referring back to FIG. 7, the application of electrosurgical energy to the electrodes disposed within the gas conduits may be changed to achieve a different scanning pattern. The output stage having a first predetermined phase angle may be applied to the electrodes at gas conduits 316-1 and 316-4, while applying energy to the electrodes at gas conduits 316-2 and 316-3 at the predetermined phase angle plus a shift of up to 180 degrees. Then, by applying the same differential gas flow waveforms as shown in FIG. 8A, a similar 2D raster scan will be created as in FIG. 8A, except in this embodiment the 2D raster scan will be rotated at a 45 degree angle.

It is to be appreciated that the above embodiments and methods may be employed in, but not limited to, procedures such as endometriosis, adhesiolysis, oopherectomy, vascular general surgery, bowel resection, and radical nectosection, and furthermore may be used in treatments for, but not limited to, abdominal aortic aneurysms, cardio-thoracic bleeding, deviated septums, hemorrhoids, prostate and snoring. It is to be understood that this listing is merely illustrative and in no way meant to be exhaustive.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical system for generating a plasma stream on a surgical site of a patient, the system comprising:
    an electrosurgical generator, coupled to an electrical power source, that generates electrosurgical energy;
    a plasma generator including at least first and second gas conduits with an electrode disposed within each of the first and second gas conduits, each electrode operatively coupled to the electrosurgical generator to selectively receive electrosurgical energy therefrom, the electrosurgical energy supplied to each electrode having a predetermined phase shift relative to each other,
    wherein the electrodes at least partially ionizes a carrier gas fed to the at least first and second gas conduits to create a single plasma discharge; and
    a flow controller coupled to the at least first and second gas conduits to modulate the rate of the carrier gas from a gas source to the at least first and second gas conduits such that the plasma discharge scans the surgical site without moving the plasma generator.

2. The electrosurgical system as in claim 1, wherein the predetermined phase shift is adjustable.

3. The electrosurgical system as in claim 2, wherein the predetermined phase shift is approximately 180 degrees.

4. The electrosurgical system as in claim 1, wherein the electrosurgical generator further comprises first and second output stages, each output stage coupled to an individual electrode.

5. The electrosurgical system as in claim 4, wherein each of the first and second output stages includes an adjustable oscillating circuit for selecting a phase angle of the electrosurgical energy being supplied therefrom.

6. The electrosurgical system as in claim 4, wherein the electrosurgical generator further comprises:
    an oscillator for providing electrosurgical energy at a first predetermined phase angle to the first output stage and a variable delay circuit; and
    the variable delay circuit for providing electrosurgical energy at a second predetermined phase angle to the second output stage, wherein a difference in the first and second predetermined phase angles determines the predetermined phase shift.

7. The electrosurgical system as in claim 4, wherein each of the first and second output stages includes a transformer where a secondary windings of one of the transformers is reversed creating a fixed 180 degrees phase shift.

8. The electrosurgical system as in claim 1, wherein the flow controller is configured to independently vary the flow rate to each of the at least first and second gas conduits.

9. The electrosurgical system as in claim 8, wherein the flow controller is configured to fix the flow rate to the at least one first gas conduit and vary the flow rate to the at least second gas conduit.

10. The electrosurgical system as in claim 1, wherein the plasma generator includes a plurality of gas conduits with an electrode disposed within each gas conduit, wherein pairs of electrodes are selectively energized with electrosurgical energy having a predetermined phase shift relative to each other.

11. An electrosurgical system for generating a plasma stream on a surgical site of a patient, the system comprising:
    an electrosurgical generator, coupled to an electrical power source, that generates electrosurgical energy;
    a plasma generator including at least first and second gas conduit pairs with an electrode disposed within each gas conduit forming at least first and second electrode pairs, each gas conduit of the gas conduit pair being arranged diametrically opposite the other gas conduit of the gas conduit pair about a central point, each electrode operatively coupled to the electrosurgical generator to selectively receive electrosurgical energy therefrom, the electrosurgical energy supplied to each electrode pair having a predetermined phase shift relative to each other,
    wherein the electrodes at least partially ionizes a carrier gas fed to the at least first and second gas conduit pairs to create a single plasma discharge; and
    a flow controller coupled to the at least first and second gas conduit pairs to modulate the flow rate of the carrier gas from a gas source to the at least first and second gas conduit pairs such that the plasma discharge scans the surgical site without moving the plasma generator.

12. The electrosurgical system as in claim 11, wherein the predetermined phase shift is adjustable.

13. The electrosurgical system as in claim 12, wherein the predetermined phase shift is approximately 180 degrees.

14. The electrosurgical system as in claim 11, wherein the flow controller is configured to apply a first triangular gas flow waveform to the at least first gas conduit pair and a second triangular gas flow waveform to the at least second gas conduit pair, wherein the first triangular gas flow waveform is multiple of the second triangular waveform pair resulting in a raster scan of the plasma discharge.

15. The electrosurgical system as in claim 11, wherein the flow controller is configured to apply a first sine gas flow waveform of increasing amplitude to the at least first gas conduit pair and a second sine gas flow waveform of increasing amplitude to the at least second gas conduit pair, wherein the second sine gas flow waveform is shifted a predetermined number of degrees resulting in an increasingly outward spiral scan of the plasma discharge.

16. The electrosurgical system as in claim 15, wherein the predetermined number of degrees is about 90 degrees.

17. A plasma generator for generating a plasma stream on a surgical site of a patient, the system comprising:
    at least first and second gas conduits with an electrode disposed within each of the first and second gas conduits, each electrode configured to be coupled to an electrosurgical generator to selectively receive electrosurgical energy therefrom, the electrosurgical energy supplied to each electrode having a predetermined phase shift relative to each other, wherein the electrodes at least partially ionizes a carrier gas fed to the at least first and second gas conduits to create a single plasma discharge; and a flow controller coupled to the at least first and second gas conduits to modulate the flow rate of the carrier gass from a gas source to the at least first and second gas conduits such that the plasma discharge scans the surgical site without moving the plasma generator.

18. The plasma generator as in claim 17, wherein the flow controller is configured to independently vary the flow rate to each of the at least first and second gas conduits.

19. The plasma generator as in claim 18, wherein the flow controller is configured to fix the flow rate to the at least one first gas conduit and vary the flow rate to the at least second gas conduit.

20. The plasma generator as in claim 17, further comprising a plurality of gas conduits with an electrode disposed within each gas conduit, wherein pairs of electrodes are selectively energized with electrosurgical energy having a predetermined phase shift relative to each other.

21. The plasma generator as in claim 17, further comprising at least first and second gas conduit pairs with an electrode disposed within each gas conduit forming at least first and second electrode pairs, each gas conduit of the gas conduit pair being arranged diametrically opposite the other gas conduit of the gas conduit pair about a central point, each electrode configured to be coupled to the electrosurgical generator to selectively receive electrosurgical energy therefrom, the electrosurgical energy supplied to each electrode pair having a predetermined phase shift relative to each other.

22. A method for generating a plasma stream on a surgical site of a patient, the method comprising:

providing a plasma generator including at least first and second gas conduits with an electrode disposed within each of the first and second gas conduits;

supplying electrosurgical energy to each electrode, the electrosurgical energy supplied to each electrode having a predetermined phase shift relative to each other, wherein the electrodes at least partially ionizes a carrier gas fed to the at least first and second gas conduits to create a single plasma discharge, and modulating a flow rate of the carrier gas from a gas source to the at least first and second gas conduits such that the plasma discharge scans the surgical site without moving the plasma generator.

23. The method as in claim 22, wherein the predetermined phase shift is adjustable.

24. The method as in claim 23, wherein the predetermined phase shift is approximately 180 degrees.

25. The method as in claim 22, further comprising independently varying the flow rate to each of the at least first and second gas conduits.

26. The method as in claim 25, further comprising fixing the flow rate to the at least one first gas conduit and varying the flow rate to the at least second gas conduit.

27. The method as in claim 22, wherein the plasma generator includes a plurality of gas conduits with an electrode disposed within each gas conduit, further comprising selectively energizing pairs of electrodes with electrosurgical energy having a predetermined phase shift relative to each other.

28. The method as in claim 22, wherein the plasma generator includes at least first and second gas conduit pairs with an electrode disposed within each gas conduit forming at least first and second electrode pairs, each gas conduit of the gas conduit pair being arranged diametrically opposite the other gas conduit of the gas conduit pair about a central point, further comprising supplying the electrosurgical energy to each electrode pair having a predetermined phase shift relative to each other electrode pair.

29. The method as in claim 28, further comprising:

applying a first triangular gas flow waveform to the at least first gas conduit pair; and applying a second triangular gas flow waveform to the at least second gas conduit pair, wherein the first triangular gas flow waveform is multiple of the second triangular waveform pair resulting in a raster scan of the plasma discharge.

30. The method as in claim 28, further comprising:

applying a first sine gas flow waveform of increasing amplitude to the at least first gas conduit pair; and applying a second sine gas flow waveform of increasing amplitude to the at least second gas conduit pair, wherein the second sine gas flow waveform is shifted a predetermined number of degrees resulting in an increasingly outward spiral scan of the plasma discharge.

* * * * *